(12) United States Patent
Boulanger et al.

(10) Patent No.: US 10,974,003 B2
(45) Date of Patent: Apr. 13, 2021

(54) RESUSCITATION BAG WITH MONITORING CAPABILITIES

(71) Applicants: Air Liquid Santé (International), Paris (FR); Air Liquide Medical Systems, Antony (FR)

(72) Inventors: Thierry Boulanger, Media, PA (US); Jean-Marc Giner, Puteaux (FR); Jean-Christophe Richard, Antony (FR); Marceau Rigollot, Montrouge (FR)

(73) Assignees: Air Liquide Medical Systems S.A., Antony (FR); Air Liquide Santé (International), Paris (FR)

( * ) Notice: Subject to any disclaimer, the term of this patent is extended or adjusted under 35 U.S.C. 154(b) by 319 days.

(21) Appl. No.: 16/201,090

(22) Filed: Nov. 27, 2018

(65) Prior Publication Data

US 2019/0160241 A1    May 30, 2019

Related U.S. Application Data

(60) Provisional application No. 62/591,293, filed on Nov. 28, 2017.

(51) Int. Cl.
*A61M 16/00* (2006.01)
*A61M 16/20* (2006.01)
*A61M 16/06* (2006.01)

(52) U.S. Cl.
CPC ........ *A61M 16/0084* (2014.02); *A61M 16/00* (2013.01); *A61M 16/0078* (2013.01);
(Continued)

(58) Field of Classification Search
CPC .............. A61M 16/00; A61M 16/0003; A61M 16/0078; A61M 16/0084; A61M 16/01;
(Continued)

(56) References Cited

U.S. PATENT DOCUMENTS

| 5,427,091 A | 6/1995 | Phillips |
| 2007/0267019 A1* | 11/2007 | Lugtigheid ......... A61M 16/208 128/205.13 |

(Continued)

FOREIGN PATENT DOCUMENTS

| WO | WO 2017 096286 | 6/2017 |
| WO | WO 2019 001751 | 1/2019 |
| WO | WO 2019 001752 | 1/2019 |

OTHER PUBLICATIONS

European Search Report for corresponding EP 18198719, dated Mar. 29, 2020.

*Primary Examiner* — Joseph D. Boecker
(74) *Attorney, Agent, or Firm* — Allen E. White

(57) ABSTRACT

The specification describes an artificial resuscitation bag (5) having (i) a deformable bag (54) with a gas inlet (54A) and a gas outlet (54B), (ii) a pneumatic control valve (50) comprising an exhaust port (50c) adapted for controlling the flow of gas exiting to the atmosphere through said exhaust port (50c), and (iii) a monitoring module (60), operably connected to the pneumatic control valve (50) and having an absolute pressure sensor (60d) for measuring at least an absolute pressure (Pabs) in the inner compartment (50f) of the pneumatic control valve (50) and for transmitting at least an absolute pressure signal to a central processing unit (60c) and an ambient pressure sensor (60b) for measuring at least an atmospheric pressure (Patm) and for transmitting at least an atmospheric pressure signal to the central processing unit (60c).

13 Claims, 13 Drawing Sheets

(52) U.S. Cl.
CPC ........ *A61M 16/024* (2017.08); *A61M 16/202* (2014.02); *A61M 16/206* (2014.02); *A61M 16/209* (2014.02); *A61M 16/06* (2013.01); *A61M 16/208* (2013.01); *A61M 2016/0027* (2013.01); *A61M 2202/0208* (2013.01); *A61M 2205/3341* (2013.01); *A61M 2205/3358* (2013.01); *A61M 2205/8206* (2013.01)

(58) Field of Classification Search
CPC .... A61M 16/024; A61M 16/06; A61M 16/08; A61M 16/0816; A61M 16/0833; A61M 16/0875; A61M 16/20; A61M 16/202; A61M 16/204; A61M 16/205; A61M 16/206; A61M 16/208; A61M 16/209; A61M 2016/0027; A61M 2205/3341; A61M 2205/3358
See application file for complete search history.

(56) References Cited

U.S. PATENT DOCUMENTS

| | | | |
|---|---|---|---|
| 2008/0314386 A1* | 12/2008 | Myklebust | A61M 16/0084 128/205.15 |
| 2017/0157348 A1* | 6/2017 | Gillespie | A61M 16/0003 |
| 2020/0171253 A1* | 6/2020 | Boulanger | A61M 16/0875 |

* cited by examiner

RESUSCITATION BAG WITH MONITORING CAPABILITIES

CROSS REFERENCE TO RELATED APPLICATION

This application claims the benefit of priority under 35 U.S.C. 119 (a) and (b) to US Provisional Patent Application No. 62/591,293 filed Nov. 28, 2017, the entire contents of which are incorporated herein by reference.

BACKGROUND

The present invention relates to an artificial respiration device with monitoring capabilities, namely an artificial resuscitation bag that can be used for resuscitating a person, i.e. a patient, in state of cardiac arrest, and an installation for resuscitating a person in state of cardiac arrest comprising such an artificial resuscitation bag.

Cardiac arrest is a condition affecting many people every year with a very poor prognosis.

One of the main lifesaving actions is the realization of thoracic compressions or 'TCs' along with brief periods of lung ventilation with a resuscitation bag. TCs are successive compressions and decompressions exerted by a rescuer, such as a medical staff or any other person, on the thoracic cage of the person, i.e. the patient, in cardiac arrest.

TCs aim at partially restoring inspiration and expiration phases and therefore gas exchanges in the lungs, as well as promoting or restoring a blood circulation toward the brain of the patient.

As these compressions and decompressions mobilize only small volumes of gas in and out of the patient's airways, it is advocated to perform regularly additional gas insufflations to bring fresh $O_2$-containing gas into the lungs, thereby enhancing the gas exchanges in the lungs.

Usually, fresh $O_2$-containing gas is delivered by a resuscitation bag fed by an oxygen source and connected to the patient through a respiratory interface, typically a facial mask, a laryngeal mask, an endotracheal tube or any other suitable device.

To date, it is recommended to interpose 2 insufflations every 30 chest compressions, whereas the ideal rate of compressions, according to international guidelines, should be of between 100 and 120 compressions per minute (c/min).

However, several studies have shown that it is difficult for rescuers to correctly perform the resuscitation sequence.

One reason is the inability with current solutions to provide a feedback to the rescuers of how well the TCs and insufflations are performed. During TCs the pressure at the patient's airways is fluctuating between positive pressures (during compression) and sub-atmospheric pressures (during decompression) and the frequency of these fluctuations reflects the rate at which these compressions are performed.

During the insufflations phases with the resuscitation bag, rescuers are particularly concerned by the generated pressure level, as excessive and potentially harmful pressure levels should be avoided in the lungs.

In other words, providing the information of the pressure level in the patient's airway during insufflations and the rate at which thoracic compressions are performed would be of great value for the rescuers, for instance a medical staff, performing a cardiac resuscitation to a person in state of cardiac arrest.

SUMMARY

Hence, one goal of the present invention to provide an inexpensive, unobtrusive and reusable monitoring module that is arranged on or that can be preferably plugged to a resuscitation bag for providing the pressure level in the patient's airway to the rescuer, and/or the rate at which thoracic compressions are performed, while a cardiac resuscitation with TCs is operated.

A solution according to the present invention concerns an artificial resuscitation bag comprising:
  a deformable bag comprising a gas inlet and a gas outlet,
  a gas conduit in fluid communication with the gas outlet of the deformable bag, and
  a pneumatic control valve comprising an exhaust port for controlling the flow of gas exiting to the atmosphere through said exhaust port, and further comprising an inner compartment,
  a first one-way valve arranged in the gas conduit between the gas outlet of the deformable bag, and the pneumatic control valve and
  a derivation conduct having:
    i) a first end fluidly connected to the gas conduit, between the gas outlet of the deformable bag and the first one-way valve, and
    ii) a second end fluidly connected to the inner compartment of the pneumatic control valve,
and further comprising a monitoring module, arranged on the pneumatic control valve, comprising:
  an absolute pressure sensor for measuring at least an absolute pressure (Pabs) in the inner compartment of the pneumatic control valve and for transmitting at least an absolute pressure signal to a central processing unit,
  an ambient pressure sensor for measuring at least an atmospheric pressure (Patm) and for transmitting at least an atmospheric pressure signal to a central processing unit,
  a central processing unit (60c) for:
    i) processing said absolute pressure signal and atmospheric pressure signal received from the absolute pressure sensor and from the ambient pressure sensor, and
    ii) determining at least a relative pressure (Pr) in inner compartment.

Indeed, the relative pressure (Pr) in the inner compartment of the artificial resuscitation bag of the present invention reflects the pressure level in the patient's airways during insufflations and informs the rescuer about the quality of the thoracic compressions that is operated on the patient in cardiac arrest.

Depending on the embodiment, an artificial resuscitation bag according to the present invention can comprise of one or several of the following additional features:
  the artificial resuscitation bag comprises a battery unit for electrically powering the pressure sensors and the central processing unit.
  the central processing unit calculates a relative pressure (Pr) in inner compartment using the following formula:

Pr=Pabs−Patm wherein:
    Pr represents the relative pressure,
    Patm represents the atmospheric pressure measured by the atmospheric pressure sensor,
    and Pabs represents the absolute pressure measured by the absolute pressure sensor.
  the pneumatic control valve further comprises a membrane element cooperating with the exhaust port for controlling the flow of gas exiting to the atmosphere through said exhaust port, said membrane element being arranged into the inner compartment of the pneumatic control valve.

an overpressure valve is arranged in the gas conduit.

the monitoring module is detachably fixed to the pneumatic control valve.

the monitoring module comprises an electronic board, said absolute pressure sensor, said ambient pressure sensor and said central processing unit being arranged on said electronic board.

the monitoring module is arranged on a detachable lid structure.

the inner compartment is divided into at least a first chamber and a second chamber separated by a separating wall comprising a gas passage ensuring a fluid communication between said first chamber and second chamber.

the first chamber of the inner compartment comprises the membrane element.

the second chamber of the inner compartment comprises the absolute pressure sensor.

the artificial resuscitation bag comprises a gas delivery conduit in fluid communication with the gas conduit for conveying at least part of the gas circulating into the gas conduit to a patient interface.

the patient interface comprises of a respiratory mask or a tracheal cannula.

the gas conduit conveys at least a part of the gas exiting the deformable bag through the gas outlet.

the overpressure valve is configured to vent to the atmosphere at least part of the gas present in the gas conduit, when the gas pressure in the gas conduit exceeds a given threshold-value.

the first one-way valve is configured for allowing a circulation of gas in the gas conduit only in the direction from the deformable bag toward the pneumatic control valve.

the artificial resuscitation bag further comprises of a second one-way valve arranged in a conduit in fluid communication with the gas inlet of the deformable bag.

the artificial resuscitation bag further comprises a first conduit in fluid communication with the gas inlet of the deformable bag and an oxygen line fluidly connected to said first conduit.

the artificial resuscitation bag further comprises a graphical user interface (GUI).

the graphical user interface is configured for displaying the relative pressure Pr measured in inner compartment that reflects the pressure level in the patient's airway during insufflations, thereby guiding the rescuers during the resuscitation process.

the graphical user interface is also configured for further displaying TC rate, i.e. the rate at which the thoracic compressions are performed, thereby further guiding the rescuers during the resuscitation process.

Further, the present invention also concerns an installation for resuscitating a person in state of cardiac arrest comprising:

an artificial resuscitation bag according to the present invention, and an O₂ source fluidly connected to the artificial resuscitation bag by means of an oxygen line, for providing oxygen to said artificial resuscitation bag.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
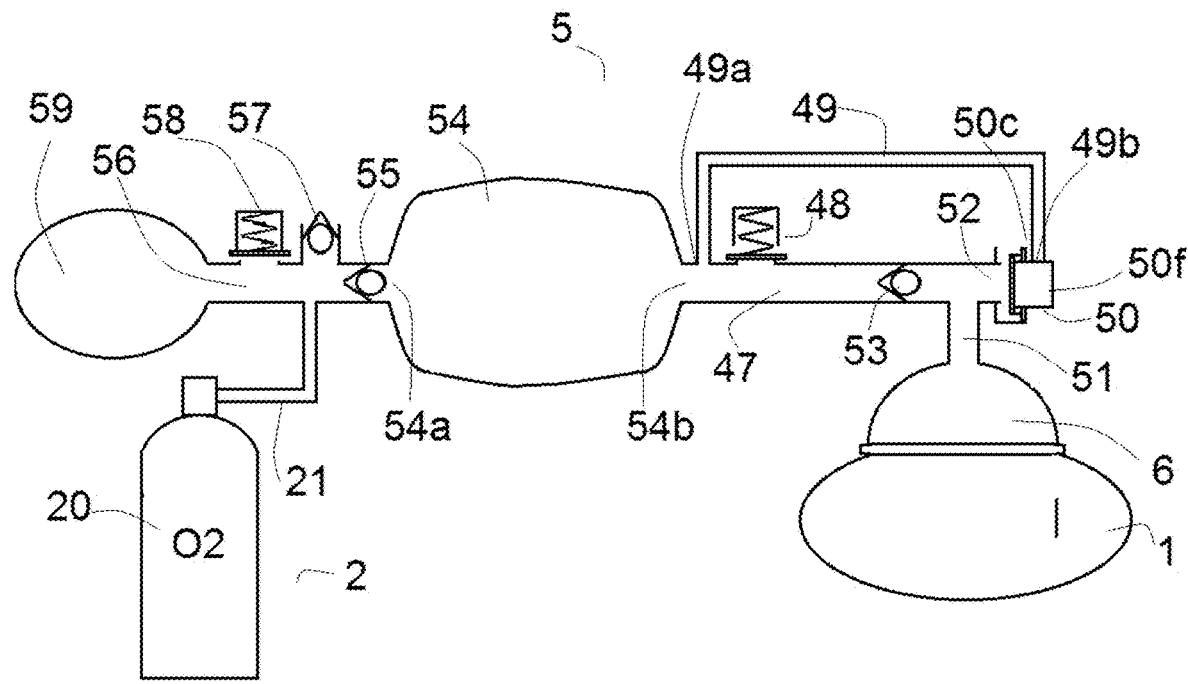
FIG. 1 is a modified resuscitation bag, background of the present invention with a cross section of a pneumatic control valve.

FIG. 1 shows a resuscitation bag 5 designed for performing a pulmonary ventilation to a person 1 in cardiac arrest, i.e. a patient, comprising a respiratory interface 6, typically a respiratory mask or any other suitable gas-delivery device, for feeding a pressurized gas, such as air/O2, to the patient 1, a flexible bag 54, a pneumatic control valve element 50 for diverting the gas in and out of the patient's airways, during insufflation and exsufflation phases, and a source of an oxygen-containing gas 2, such as a or including a gas cylinder 20 containing oxygen, which is delivered during insufflation phases by means of an oxygen line 21.

Figure 2A:
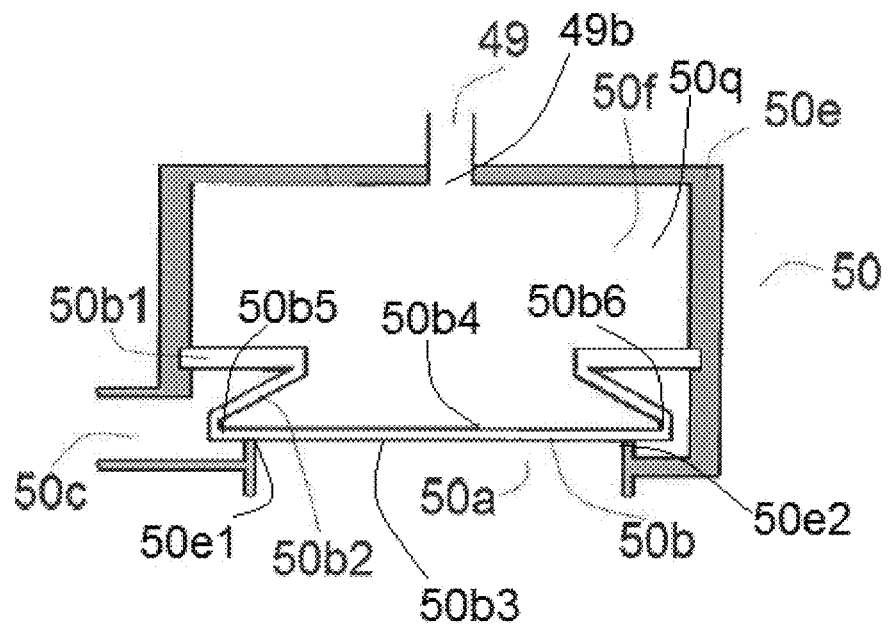
FIGS. 2A and 2B is a description of the pneumatic control valve.
Figure 2B:
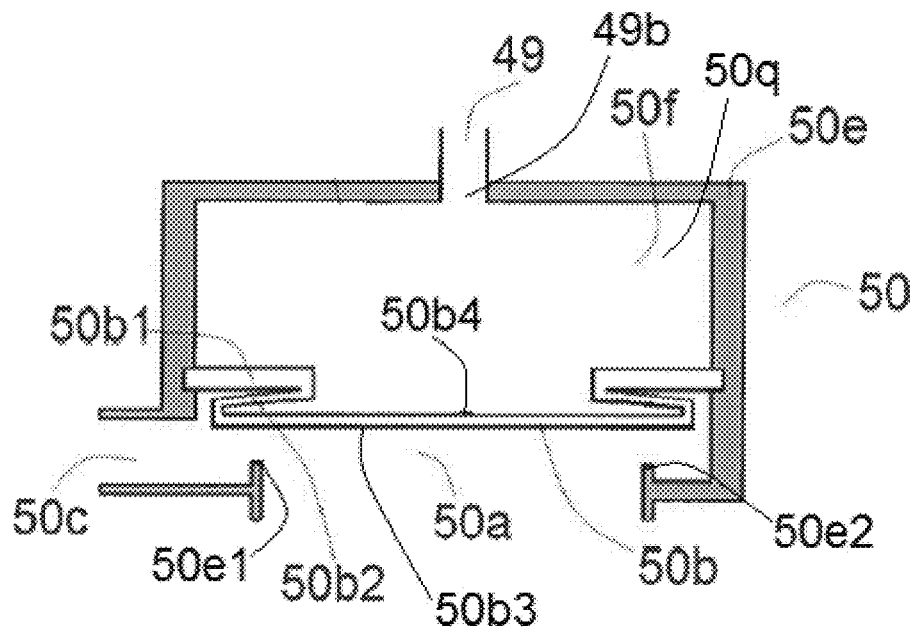

The pneumatic control valve 50 works in differential mode (cf. FIGS. 2A and 2B). The pneumatic control valve 50 comprises a deformable membrane 50b that is tightly attached by its lips 50b1 to one or several grooves in a rigid structure 50e, which forms the pneumatic control valve 50 housing. A deformable portion 50b2 of membrane 50b helps this membrane 50b move forward or backward, depending on the conditions. At rest, this membrane 50b prevents a fluidic connection between the inlet conduit 50a and outlet conduit 50c, as illustrated in FIG. 2A.

This is due to the fact that membrane 50b lays on edges 50e1 and 50e2 at rest, occluding inlet conduit 50a, and further a surface area difference exists between inner side 50b4 and outer side 50b3 of membrane 50b. Indeed, the inner side 50b4 of membrane 50b is delimited by extremity points 50b5 and 50b6, whereas the outer side of the membrane is defined as the diameter of inlet conduit 50a, delimited by edges 50e1 and 50e2. As a consequence, the surface of inner side 50b4 of membrane 50b is greater than the surface of outer side 50b3 of membrane 50b.

Considering equal pressure on both sides of membrane 50b, a positive gradient force from inner side 50b4 to outer side 50b3 is created. The mechanical strength of membrane 50b laying on edges 50e1 and 50e2 and the positive gradient force generated by the surface difference between inner side 50b4 and outer side 50b3 of membrane 50b will define an opening pressure threshold in inlet 50a which will move membrane 50b backward to allow a fluidic connection between inlet 50a and outlet 50c, as shown FIG. 2B. Depending on the size and characteristic of membrane 50b, an opening pressure as low as 5 mm $H_2O$ can be set.

The pneumatic control valve 50 of FIGS. 2A and 2B further comprises a chamber 50q, called inner compartment 50f, that is fluidically connected to a derivation conduct 49 (cf FIG. 1) comprising a first end 49A fluidly connected to the gas conduit 47, between the gas outlet 54B of the deformable bag 54 and the overpressure valve 48, and a second end 49B fluidly connected to the inner compartment 50f of the pneumatic control valve 50.

Should the derivation conduct 49 provide a positive pressure, this pressure would add a force on top of the opening pressure defined above which will in turn make it harder to open the fluidic connection between inlet 50a and outlet 50c, unless the pressure at inlet 50a follows the increase of pressure in chamber 50q, offsetting its effect.

Figure 3:
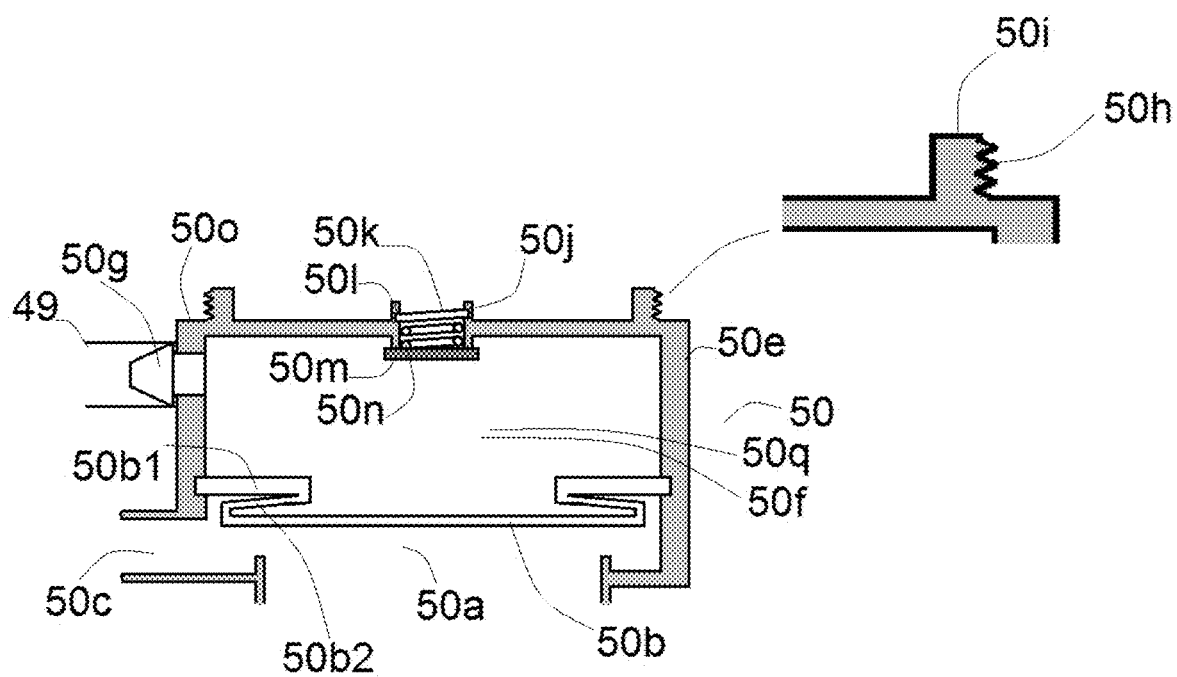
FIG. 3 is a cross section of a modified pneumatic control valve to allow the connection with a monitoring module.

FIG. 3 is a modification of said pneumatic control valve 50 allowing a subsequent connection to a preferably-detachable monitoring module.

More precisely, pneumatic control valve 50 of FIG. 3, while being similar to the pneumatic control valve of FIG. 2A, further includes:
 a threaded portion 50h for mechanical coupling with a monitoring module, and
 a membrane 50m which, at rest, prevents any leakage from inner compartment 50f.

The membrane 50m realizes a tight seal around an orifice, i.e. a gas passage 50j, delimited by a circular wall carved out in the housing 50e. A load spring 50k is, at its upper extremity, fixed to the wall 50j via groves 50l. On the other end of the load spring 50k, its extremity is tightly attached to the membrane 50m via another grove 50n. The length at rest of the load spring will determine the final position of the membrane 50m but limited by the lower extremity of the wall 50j. By selecting the right mechanical properties of the load spring 50k it is easy to have the membrane 50m in contact with the lower extremity of wall 50j therefore performing a tight seal and preventing any leak from inner compartment 50f to ambient.

Figure 4:
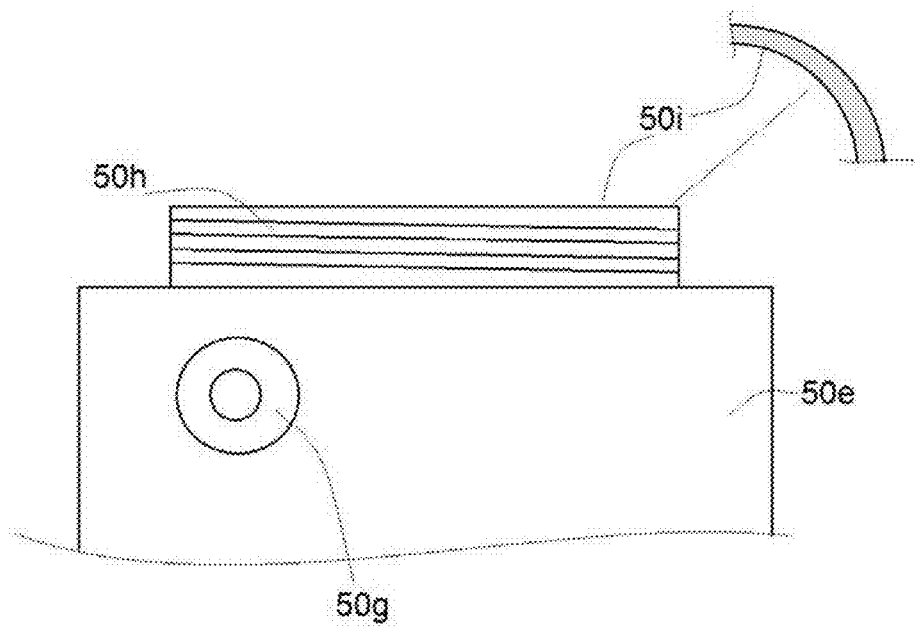
FIG. 4 is a lateral view of such pneumatic control valve.

FIG. 4 gives a better grasp of the pneumatic control valve 50 by providing a lateral view showing the housing 50e with port 50g. Its upper part is the threaded portion 50h discussed above. This threaded portion has, on its top, a specific coating 50i. Such coating is made out of a conductive material such as gold plating whose thickness is of several micrometers. It will appear obvious about the utility of this coating 50i later on.

Figure 5A:
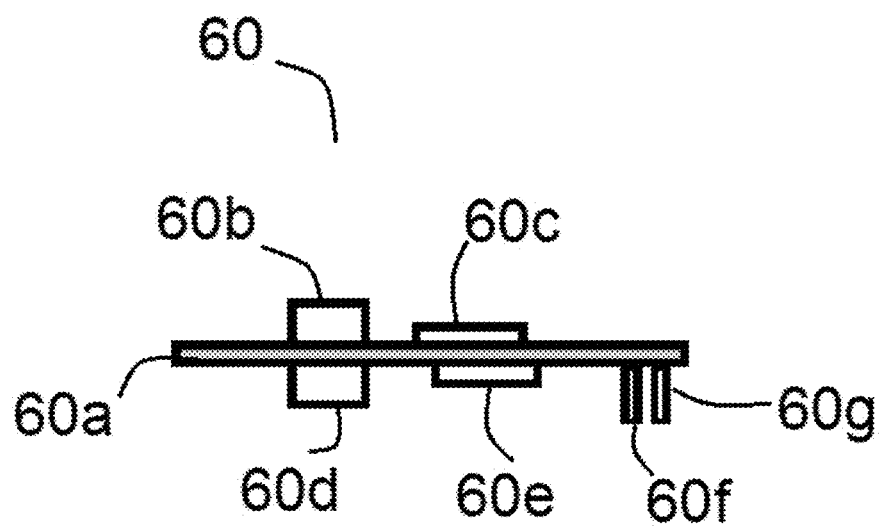
FIGS. 5A, 5B and 5C is the electronic board of the present invention which provides monitoring and communication capabilities.

FIG. 5A provides details on the electronic module 60.

Said electronic module 60 comprises an electronic board 60a on which electronic components are mounted, especially two barometric (pressure) sensors 60b and 60d, which sense the atmospheric pressure, also called absolute pressure. Those have the advantage of being inexpensive and with very low power consumption.

Many commercially available pressure sensors can be used such as a Bosch Sensortech BMP380.

Figure 5B:
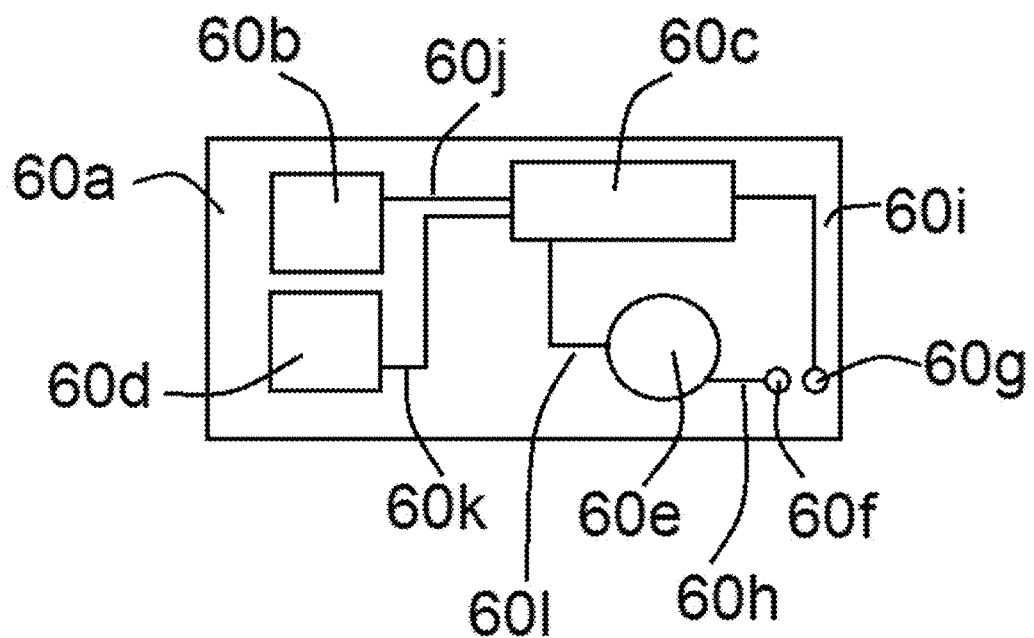

These absolute pressure sensors 60b, 60d are electrically connected to a central processing unit 60c via wire 60j and 60k respectively, as shown in FIG. 5B.

Such central processing unit 60c embeds computational capabilities for thereby processing the information, i.e. pressure signals, sent by the absolute pressure sensors 60b, 60d and can also provide means to transmit these data wirelessly, for instance by Bluetooth, so that display of the data can be done remotely, such as on a tablet or an augmented reality apparatus such as an electronic display glasses.

Powering of these different electronic components is made possible thanks to a battery 60e. This battery 60e can be of the form of a coin cell such as LiOn CR2025 or CR2032. The electrical pathway is conditioned by electrical leads 60l, on the one hand, and 60h and 60i, on the other hand, both ended by two contacts 60f, 60g.

Figure 5C:
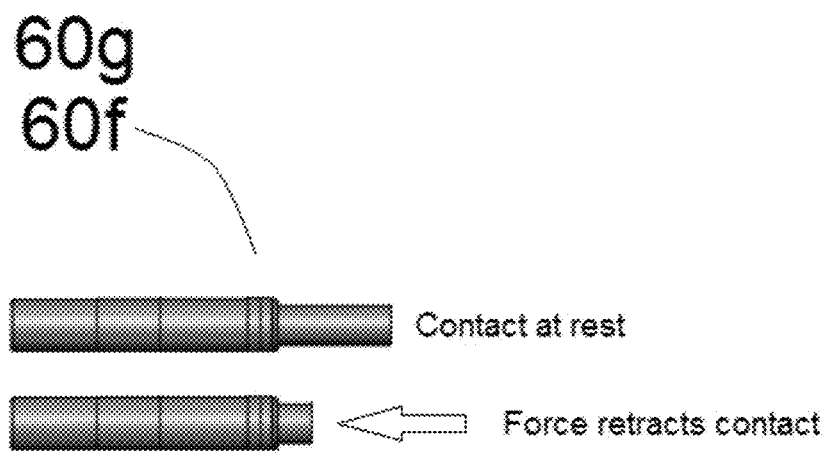

FIG. 5C shows that such contacts are compressible in a way that they have the ability to retract, when a force is applied to them. Many commercially available contacts are suitable. An Ingun HFS series is a good example of such compressible contacts.

A gap exists between the contacts 60f, 60g (FIG. 5B) and therefore the battery 60e is unable to power the different components of the electronic board 60a and especially the central unit 60c, via electrical lead 60l, which in turns powers the absolute pressure sensors 60b, 60d via leads 60j and 60k. This specificity has the advantage to save power whenever the electronic module is not in use.

Figure 6:
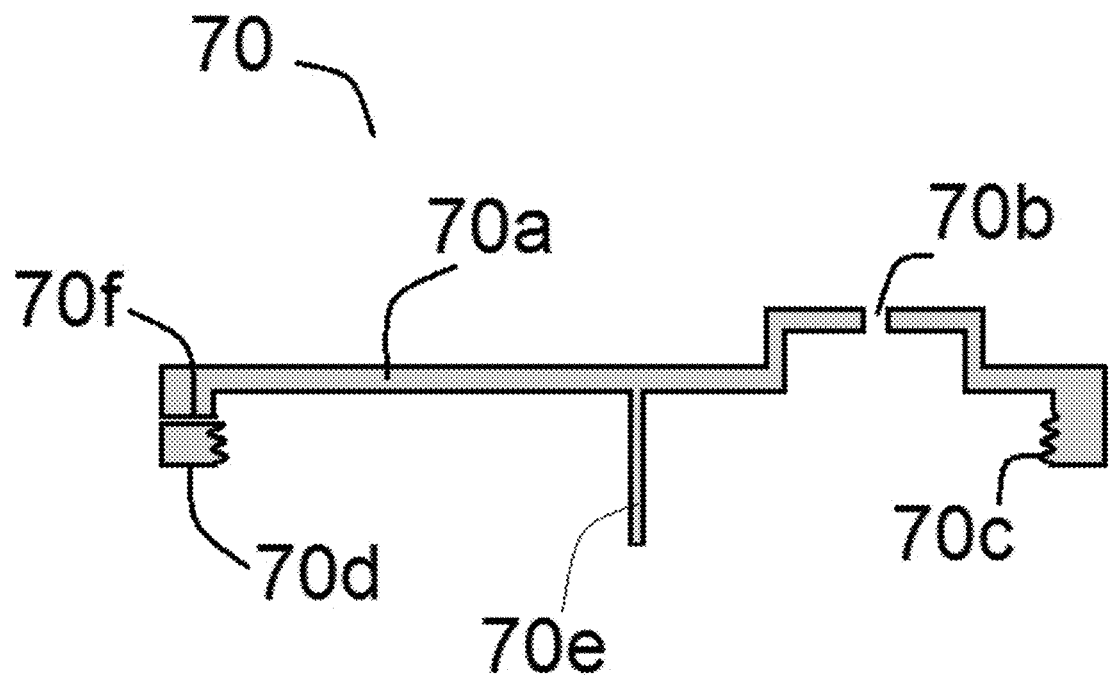
FIG. 6 is the housing of the monitoring module where the electronic board is placed (FIG. 7), FIGS. 8 to 10 describe the sequence of the connection of the monitoring module to the resuscitation bag.

FIG. 6 is a cross section of an upper detachable lid 70 or cover of the monitoring module 60 equipping the artificial resuscitation bag 5 of the present invention. In the present embodiment, the lid 70 is detachable; however, it could be also designed for being not detachable, i.e. integrally-fixed to the pneumatic control valve 50.

The upper lid 70 is made of a housing 70a comprising a threaded portion 70c (but the lid 70 could be also glued), a tip 70e and two venting orifices 70b, 70f.

Figure 7:
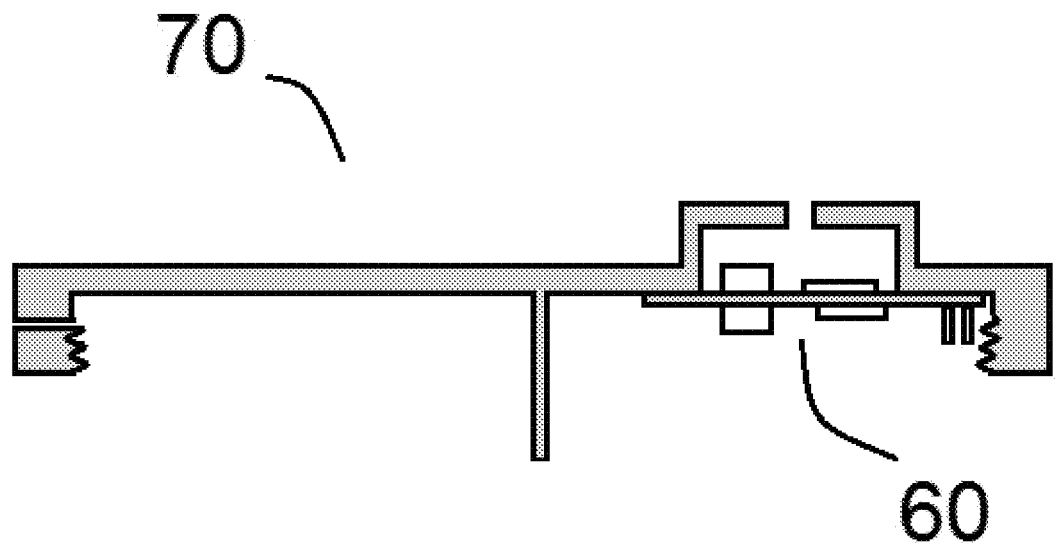

In FIG. 7 the monitoring module 60 is fixed to the detachable lid, for instance by the means of screws (not represented) and the absolute pressure sensor 60b is measuring the atmospheric pressure conditions via the venting orifice 70b.

Figure 8:
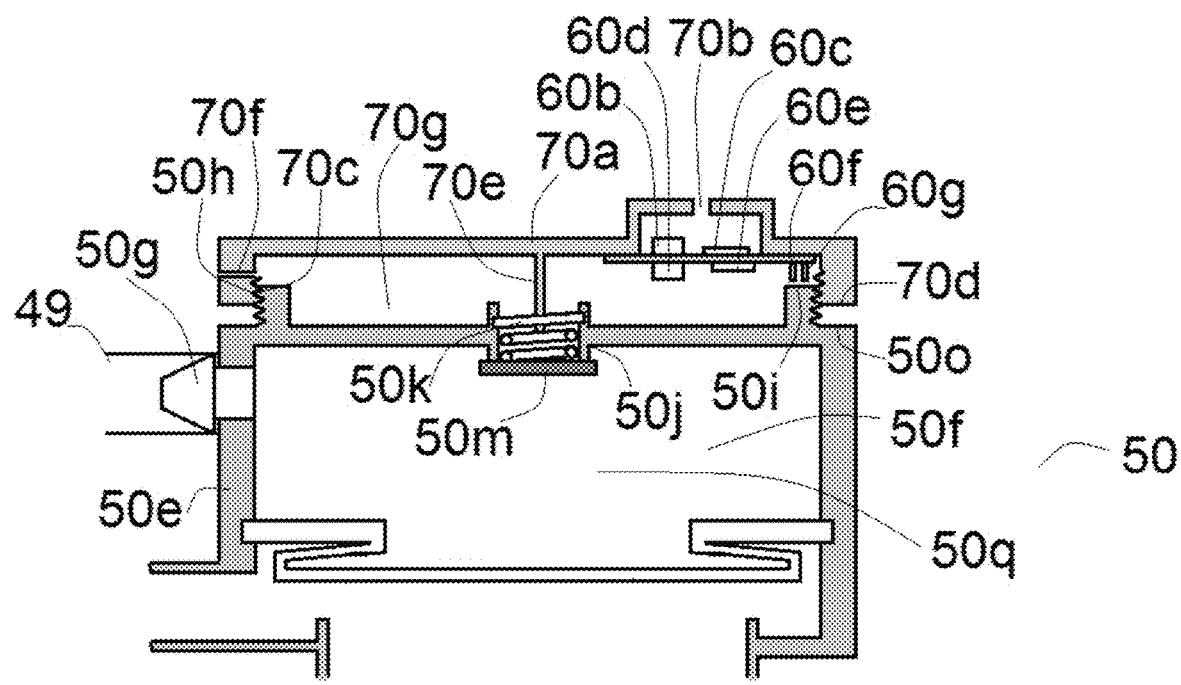
Figure 9:
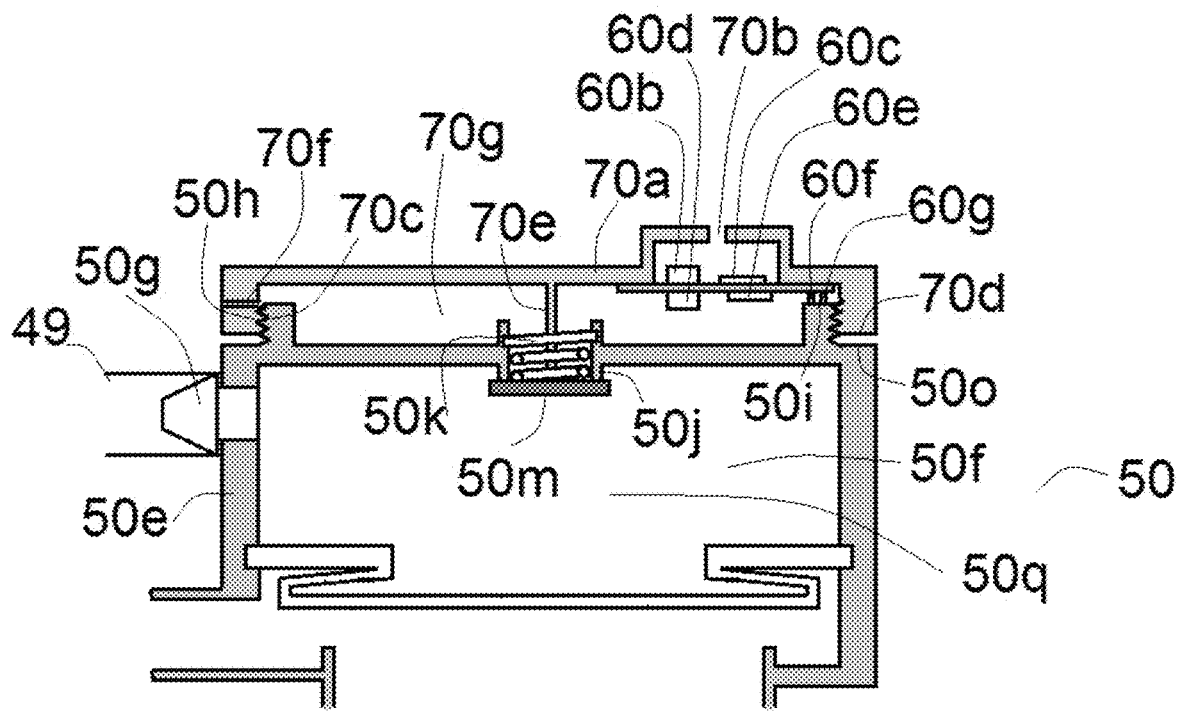
Figure 10:
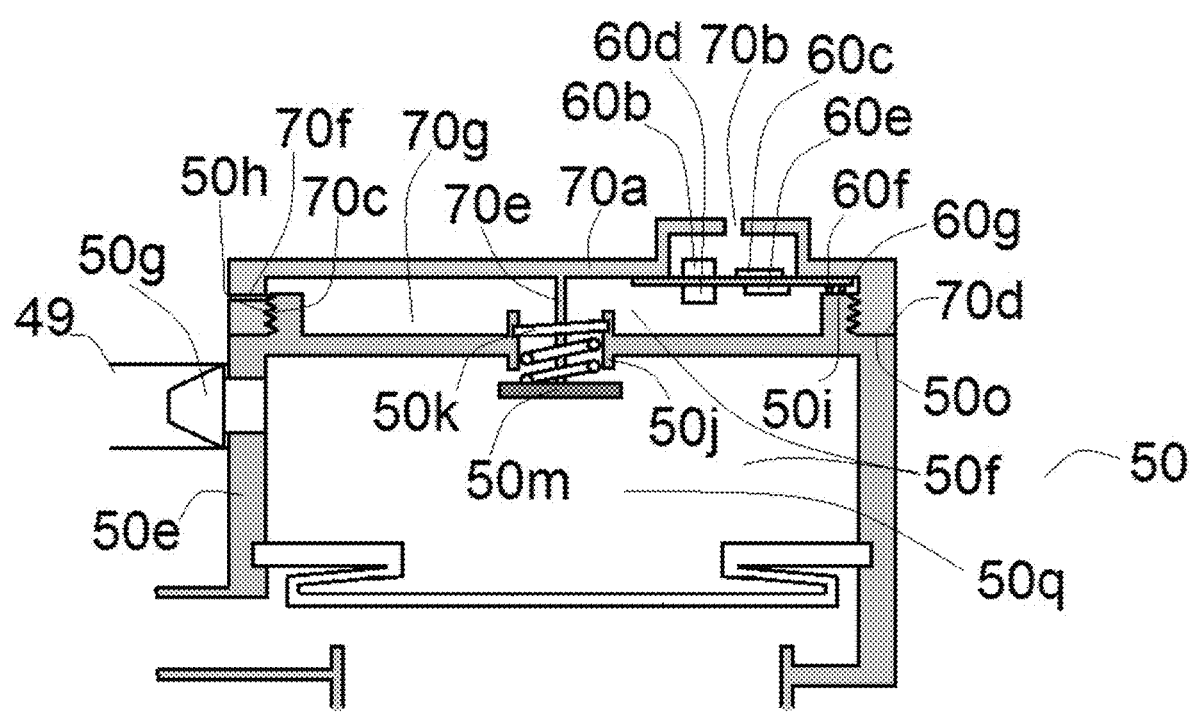

FIGS. 8 to 10 allow better understanding the connection of the monitoring module 60 to the pneumatic control valve 50 so as to provide monitoring capabilities to the resuscitation bag 5. In FIG. 8 threaded portions 70c, 50h of upper lid 70 and pneumatic control valve 50 come into contact and perform a mechanical coupling between them. At this stage, the venting orifice 70f makes a fluidic connection between the atmospheric pressure conditions and chamber 70g so that said atmospheric pressure conditions are present in said chamber 70g.

Meanwhile, tip 70e is inserted in the orifice delimited by wall 50j without any influence on the position of membrane 50m so that tightness is still respected and that no fluidic connection exists between a first chamber 50q and a second chamber 70g of inner compartment 50f.

The inner compartment 50f is divided into a first chamber 50q and a second chamber 70g separated by a separating wall 50j comprising a gas passage 50j ensuring a fluid communication between said first chamber 50q and second chamber 70g.

At this stage of the coupling, contacts 60f and 60g are however not yet in contact with the gold plating 50i on top of the threaded portion 50h. In other words, the battery 60e is still not powering the electronic components of the electronic board 60a.

In FIG. 9 the upper lid 70 is further inserted into pneumatic control valve 50 via threaded portions 50h, 70c. At this further stage of the coupling, the venting orifice 70f still makes a fluidic connection between the atmospheric pressure conditions and chamber 70g so that said atmospheric pressure conditions are present in said chamber 70g. In other words, absolute pressure sensors 60b and 60d are placed under the same atmospheric conditions since both venting orifice 70b and 70f connect said absolute pressure sensors 60b and 60d to ambient, e.g. atmospheric pressure.

Meanwhile, tip 70e is inserted in the orifice delimited by wall 50j, still without any influence on the position of membrane 50m so that tightness is still respected and that no fluidic connection exists between chambers 50q and 70g of inner compartment 50f. At this further stage of the coupling, contacts 60f and 60g come into contact with the gold plating 50i on top of the threaded portion 50h.

As discussed in FIGS. 5A, 5B and 5C, this creates an electrical pathway between contacts 60f, 60g and consequently between electrical leads 60l, 60h, 60i. The battery 60e therefore starts powering the electronic components of the electronic board 60a. Especially, a first phase will consist in measuring and storing the atmospheric pressure Patm in chamber 70g (called Patm_60d_initial) by the mean of absolute pressure sensor 60d which transmits the information to the central unit 60c via electric wire 60k for processing and storage. Simultaneously, the absolute pressure sensor 60b measures the same atmospheric pressure Patm via venting orifice 70b (called Patm_60b_initial) and will send information via electric wire 60j to central processing unit 60c for processing and storage.

This first phase is called the zeroing phase.

In FIG. 10 the monitoring module is in place, meaning that the lower surface 70d of the threaded portion 70c of upper lid 70 is in contact with the surface 50o of pneumatic control valve 50. In this position the venting orifice 70f is occluded by threaded portion 50h and therefore the fluidic connection between chamber 70g and ambient is no longer valid.

As can be understood, the contacts 60f, 60g are still in contact with gold plated portion 50i and therefore the coin cell battery 60e is still able to power the different components of electronic board 60a.

In this phase, the tip 70e of upper lid 70 is further inserted in orifice delimited by walls 50j and exerts a constraint on membrane 50m and, as a consequence, creates a fluidic connection between chambers 50q and 70g of inner compartment 50f. The absolute pressure P50q in chamber 50q is therefore instantaneously transmitted to chamber 70g where the absolute pressure sensor 60d can perform a measurement and send the information to central processing unit 60c via electrical wire 60k. From now, the pressure sensor 60d measures the absolute pressure in inner compartment 50f, called Pabs_60d.

The central processing unit 60c is able to calculate the relative pressure Pr in inner compartment 50f by subtracting the absolute pressure Pabs and initial atmospheric pressure Patm:

$$Pr=Pabs\_60d-Patm\_60d\_initial$$

However, the initial atmospheric pressure condition, also measured by absolute pressure sensor 60b can change over time, for instance in case of helicopter transportation.

As the atmospheric pressure changes according to the altitude, it is necessary to take this change into account to measure a robust relative pressure Pr in inner compartment 50f.

By periodically measuring the atmospheric conditions Patm_60b thanks to absolute pressure 60b (and electrical wire 60j), central unit 60c is able to calculate the real relative pressure Pr in inner compartment 50f, independently of the change of atmospheric conditions:

$$Pr=Pabs\_60d-Patm\_60d\_initial-(Patm\_60b-Patm\_60b\_initial)$$

In other words, the monitoring module 60 arranged on the pneumatic control valve 50 of an artificial resuscitation bag 5 according to the present invention, comprises an absolute pressure sensor 60d for measuring an absolute pressure Pabs in the inner compartment 50f of the pneumatic control valve 50 and for transmitting an absolute pressure signal to the central processing unit 60c, as well as an ambient pressure sensor 60b for measuring the atmospheric pressure Patm and for transmitting at least an atmospheric pressure signal to the central processing unit 60c, wherein the absolute pressure signal and atmospheric pressure signal received from the sensors 60d and 60b are processed for thereby determining the relative pressure Pr in inner compartment 50f.

Figure 11:
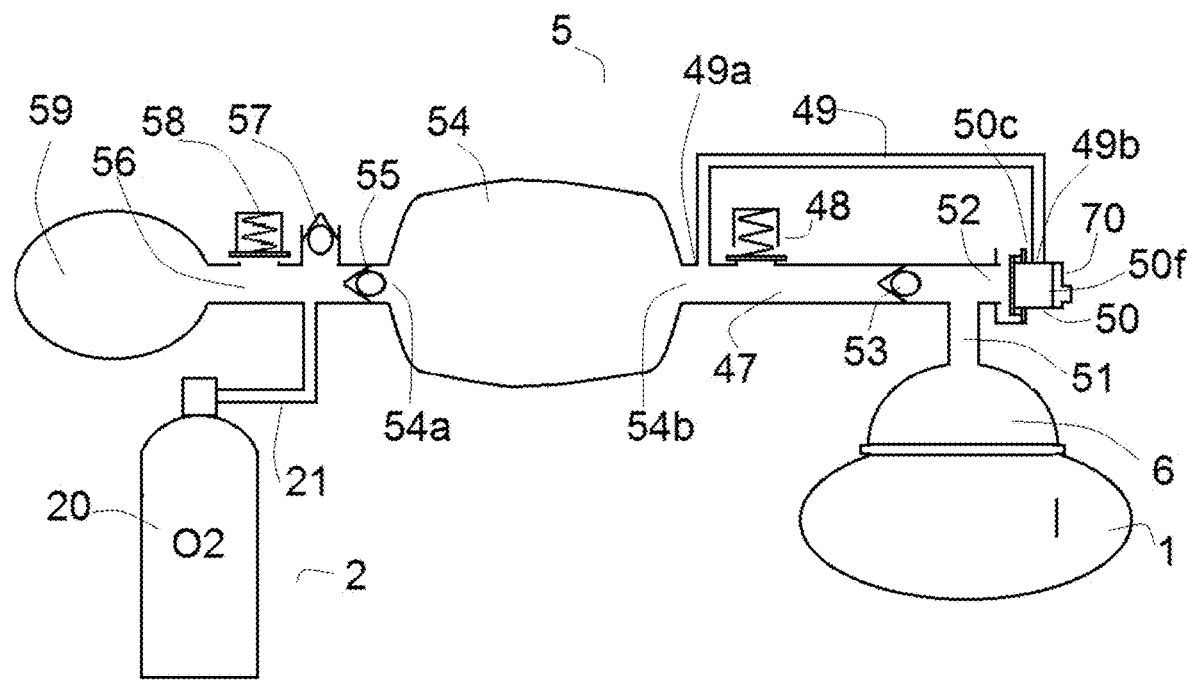
FIG. 11 is the global view of the resuscitation bag equipped with a monitoring module, FIGS. 12, 13, 14A and 14B detail the phenomenon occurring in the pneumatic control valve during a thoracic compression.

In FIG. 11, the upper lid 70 is in place on top of pneumatic control valve 50. The relative pressure Pr measured in inner compartment 50f will provide the information of the pressure level in the patient's airway during insufflations and the rate at which the thoracic compressions are performed so as to guide the rescuers during the resuscitation process.

To this end, said relative pressure Pr is displayed on a support which can be either a small display connected to the monitoring module 60 or an external support such as a smartphone display or an augmented reality apparatus such as an electronic display glasses, which are able to receive data wirelessly from the monitoring module 60, itself additionally equipped with wireless transmission capabilities.

EXAMPLES

Example 1: Monitoring Thoracic Compression Rate

Figure 12:
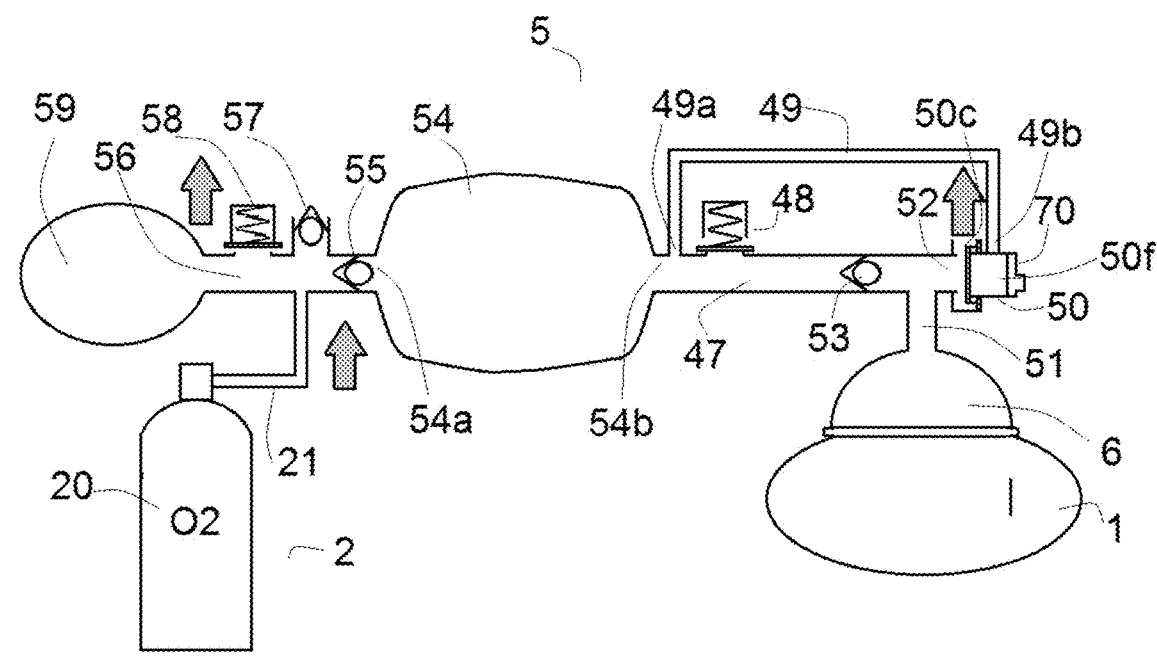
Figure 13:
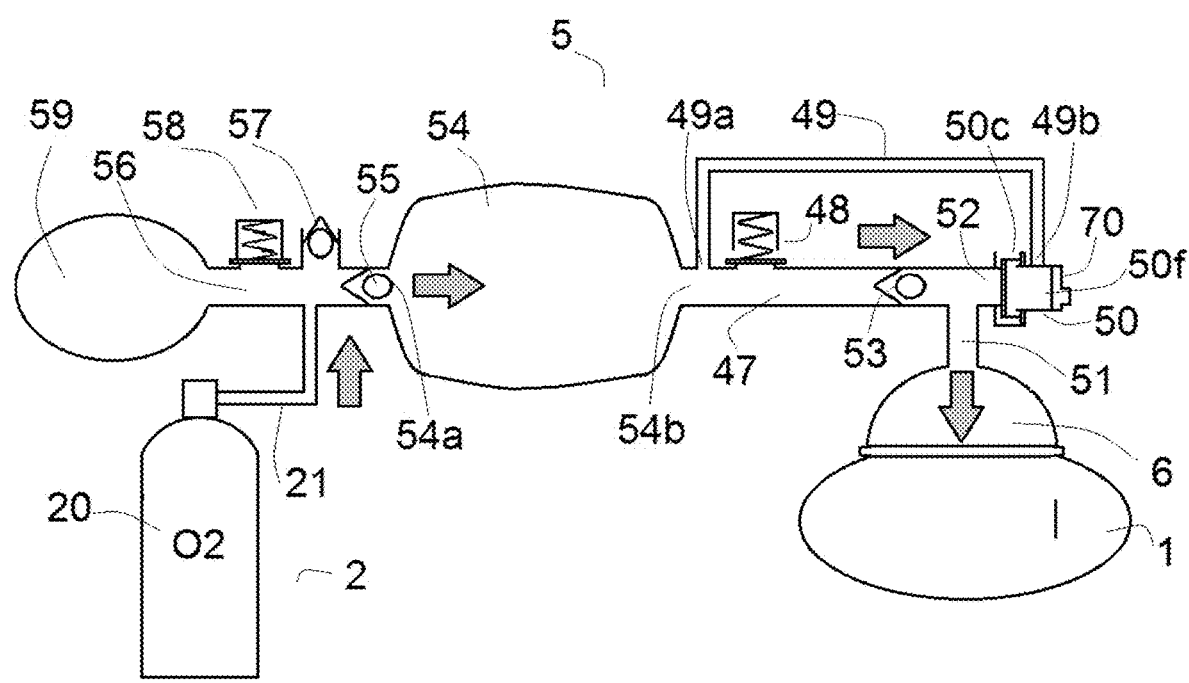

FIGS. 12 and 13 represent a sequence of TCs performed by a rescuer with the resuscitation bag 5 at rest, e.g. without any action on the bag 54. During a thoracic compression (FIG. 12) the positive pressure which is generated closes one-way valve 53 and the flow coming out of patient 1 travels into interface 6, conduits 51 and 52 to be vented to the atmosphere through pneumatic control valve 50, when such positive pressure is greater than the opening pressure of said pneumatic control valve 50.

Figure 14A:
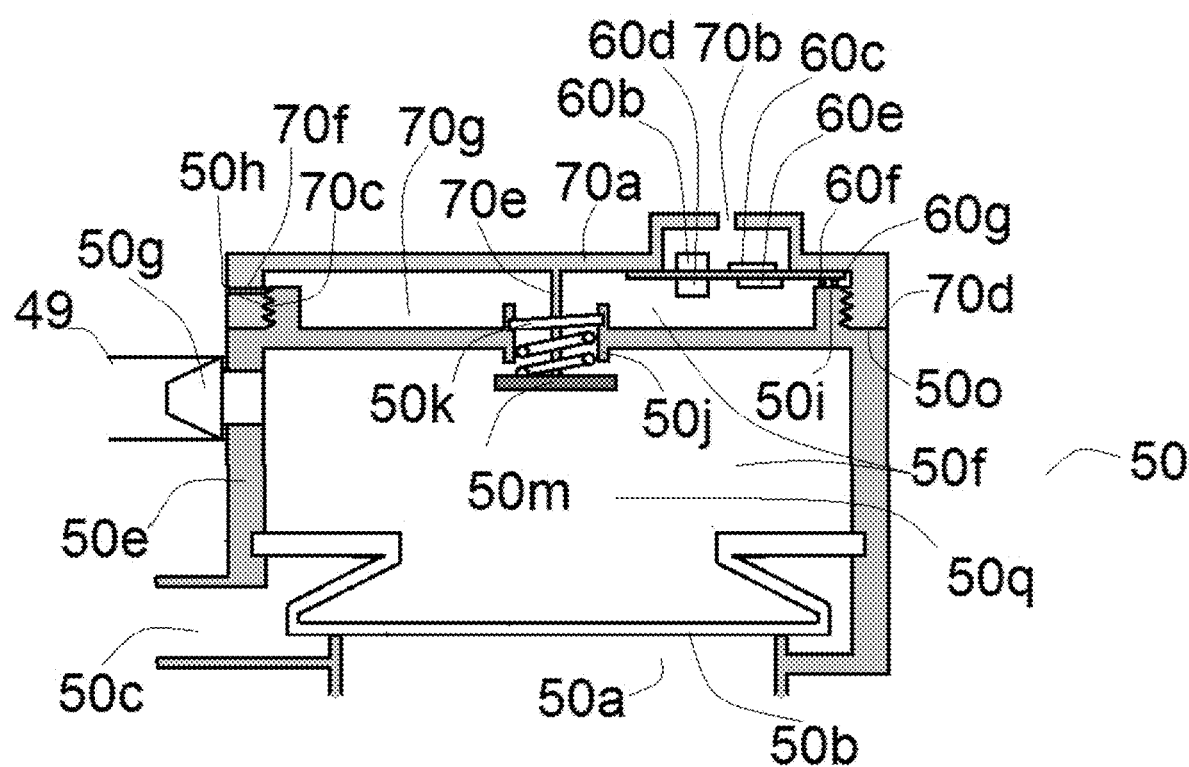
Figure 14B:
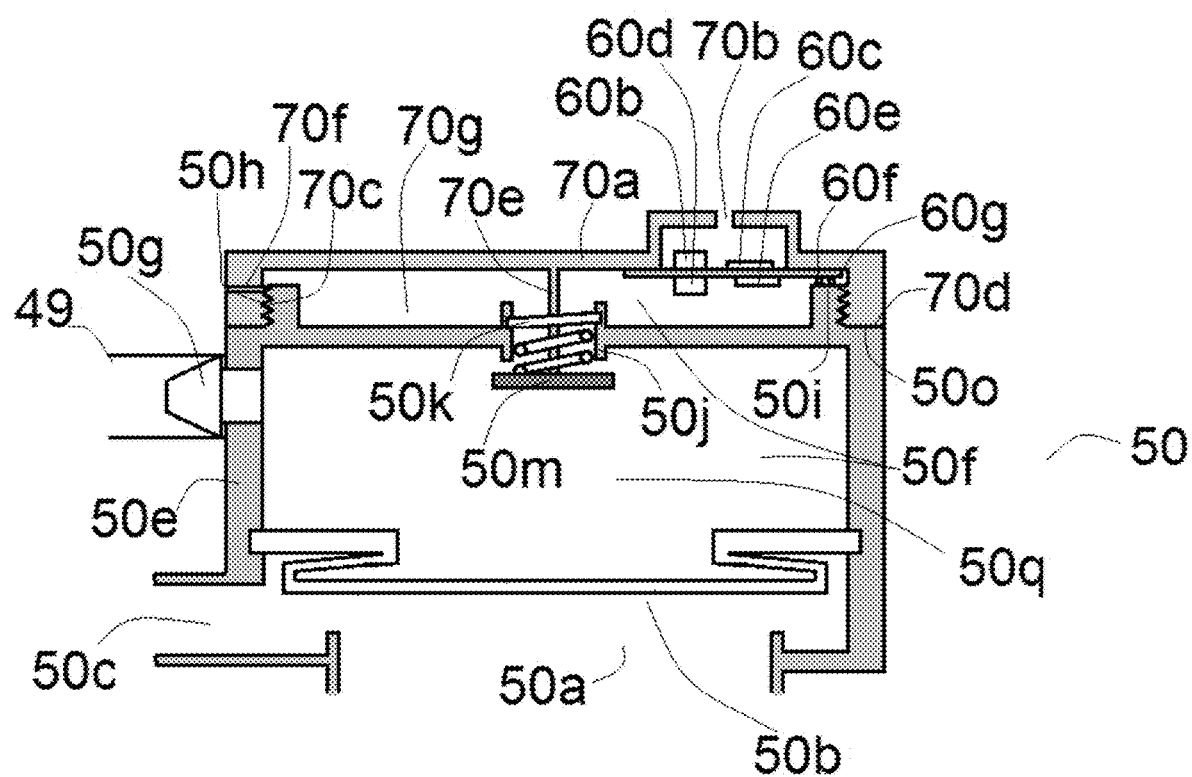

FIGS. 14A and 14B describe the transition between a closed pneumatic control valve 50 (FIG. 14A), e.g. before the thoracic compression, where the membrane 50b prevents any fluidic connection between inlet 50a and outlet 50c and an opened pneumatic control valve 50 (FIG. 14B) during the thoracic compression where the membrane 50b is pushed backward by the positive pressure and creates a fluidic connection between inlet 50a and outlet 50c in which expelled air from the patient 1 can spread through and be vented to the atmosphere.

As a consequence, the inner compartment 50f made of chambers 50q and 70g will abruptly decrease which will create a sudden rise in pressure.

This rise in pressure will tend to equalize over time with the pressure in bag 54 due to the fluidic connection between said bag 54 and inner compartment 50f of pneumatic control valve 50, operated by conduit 49, but the processing unit 60c will be able to "see" this rise of the pressure Pr, measured by the absolute pressure sensor 60d.

Similarly, after a TC follows a decompression phase (FIG. 13). The pressure in the patient's airways suddenly decreases to sub-atmospheric pressures. As a consequence, the flow of oxygen in first conduit element 56, coming from tubing 21, will be directed to the patient 1 to offset this sub-atmospheric pressure, opening the one-way valves 55 and 53, and traveling through flexible bag 54 (via inlet 54a and outlet 54b), conduits 47, 51 and interface 6. In addition, the pressure across the pneumatic control valve 50, which is between derivation conduit 49 and conduit 52, will be close to zero and as a result the pneumatic control valve 50 will be closed. In other word the inner compartment 50f of pneumatic control valve 50 will revert to its initial volume (e.g. before the thoracic compression occurred) and the pressure Pr inside said inner compartment 50f will fall down to its initial level, e.g. zero. This decrease of pressure at the patient's 1 airways, and therefore in inner compartment 50f will also be measured by the absolute pressure sensor 60d and computed by the processing unit 60c.

Figure 15:
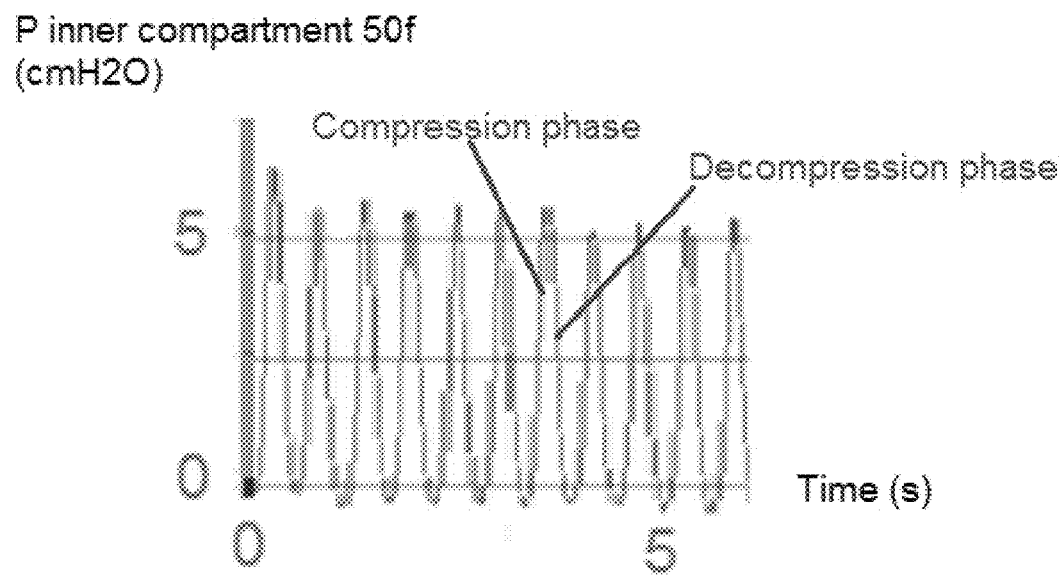
FIG. 15 illustrates pressure oscillations measured by the monitoring module during thoracic compressions.

As a consequence, such alternation during TCs will create pressure oscillations the monitoring module 60 will be able to record and process (as shown in FIG. 15). It should appear obvious to a person skilled in the art that extracting the frequency of such oscillations, e.g. the rate at which the thoracic compressions occur would involve basic signal processing algorithms, performed by processing unit 60c, and do not deserve, per say, an extensive description. However, transmitting to a display support (e.g. screen implemented on the monitoring module, smartphone display or an augmented reality apparatus such as an electronic display glasses . . . ) the rate of these compressions will be valuable to the rescuer. For example, if the measured rate of compressions falls below 100 cpm, the rescuer could be prompted to accelerate the movements to reach the target range of 100 to 120 cpm. This feedback could also help determine that the rescuer is experiencing fatigue due to this continuous effort to switch to another rescuer.

Example 2: Monitoring the Airway Pressure During Insufflation

Figure 16:
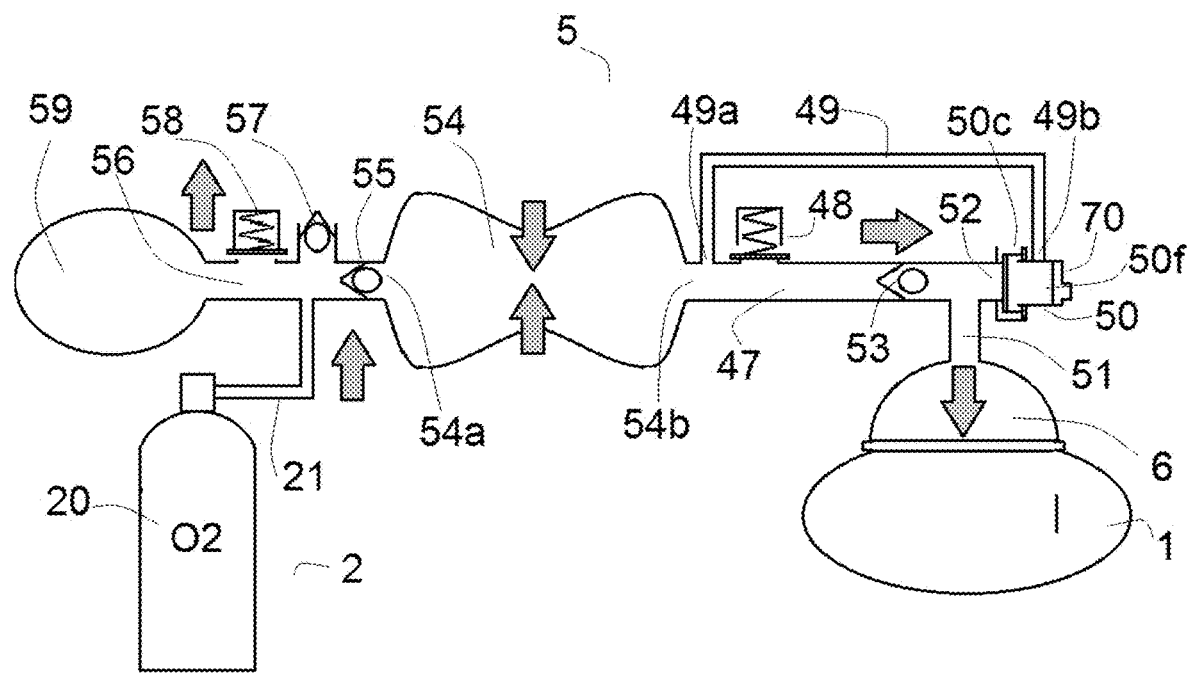
FIG. 16 illustrates the ability to measure the patient airway's pressure during an insufflation phase.

In FIG. 16 the operator starts an insufflation by squeezing the flexible bag 54, which will in turn close one-way valve 55 and open one-way valve 53. The gas will exit the bag 54 via its outlet 54b and travel into conduits 47 and 52 through one-way valve 53. Due to the minimum resistance to flow generated by these elements (e.g. less than 1 cm H2O at 60 L/min), the pressure in conduit 52 is equivalent to the pressure at the bag's 54 outlet 54b. By construction, this pressure will also spread into derivation conduit 49 at its ends 49a and 49b and therefore into inner compartment 50f. As a result, the pneumatic control valve 50 will remain closed even if the insufflation will create an increase in pressure in both sides of said pneumatic control valve 50 and all the gas exiting the bag 54 via outlet 54b will be delivered to the patient 1, via interface 6.

It is known that bag insufflations can generate dangerous pressure levels at the patient's airways due to routine absence of pressure measurement. Due to the fact that the pressure Pr in the inner compartment 50f is about the same as the pressure in conduit 52 and therefore patient's airways, transmitting this pressure to the rescuer can help stay in safe insufflation pressure levels such as below 30 cm H2O for instance.

The present invention discloses a monitoring module which can optionally be connected to a resuscitation bag and bring valuable information to the first responder such as, but not limited to, the pressure at the patient's airways during insufflations and the rate of thoracic compressions.

The selection of the absolute pressure sensor 60d is dictated by considerations on price and electrical consumption. It is one further embodiment to replace this absolute pressure sensor with a differential pressure sensor which is immune to variations of the atmospheric conditions, during aerial transportation for instance. Such pressure sensor, while more accurate and robust, is more expensive and power intensive but at least offers the user different options.

Figure 17:
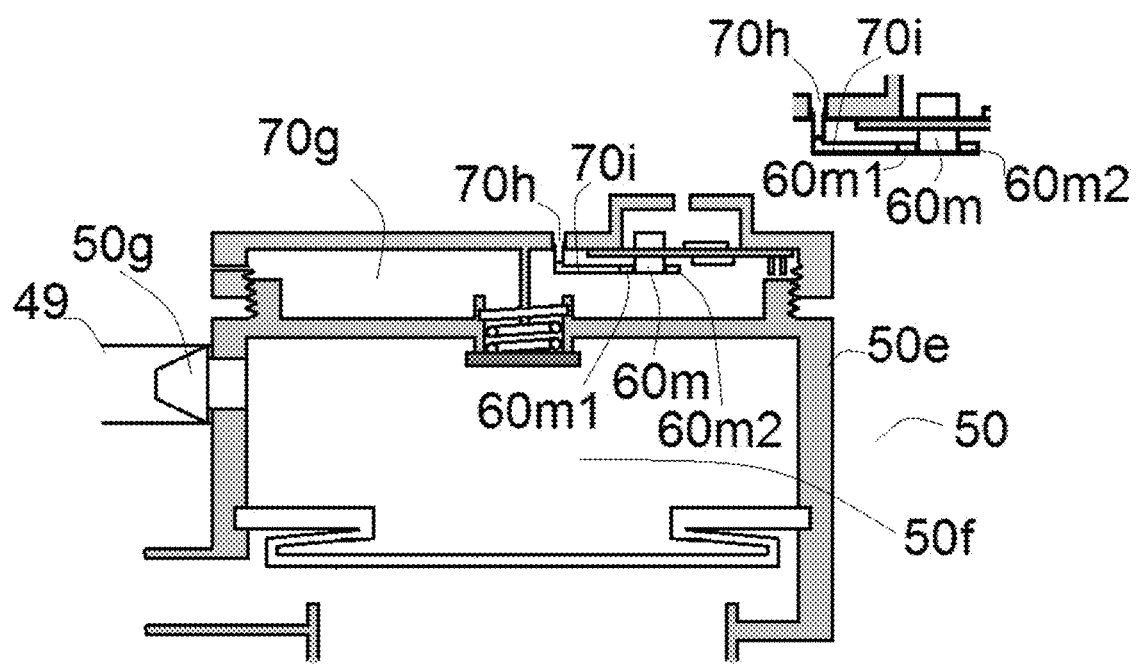
FIG. 17 is another embodiment of the monitoring module.

FIG. 17 shows such configuration where a differential pressure sensor 60m has two ports:

Port 60m1 which will sense the pressure in chamber 70g (and therefore 50f).

Port 60m2 which, fluidically connected to orifice 70h of upper lid 70 by conduit 70i will continuously sense the atmospheric condition.

By construction the sensor 60m measures the differential pressure across its ports 60m1 and 60m2 and sends them to the central processing unit 60c for further processing and display.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. An artificial resuscitation bag (5) comprising:
 a deformable bag (54) comprising a gas inlet (54A) and a gas outlet (54B),
 a gas conduit (47) in fluid communication with the gas outlet (54B) of the deformable bag (54), and
 a pneumatic control valve (50) comprising an exhaust port (50c) adapted for controlling the flow of gas exiting to the atmosphere through said exhaust port (50c), and further comprising an inner compartment (50f), a first one-way valve (53) arranged in the gas conduit (47) between the gas outlet (54B) of the deformable bag (54), and the pneumatic control valve (50) and a derivation conduct (49) having:
i) a first end (49a) fluidly connected to the gas conduit (47), between the gas outlet (54B) of the deformable bag (54) and the first one-way valve (53), and
ii) a second end (49b) fluidly connected to the inner compartment (50f) of the pneumatic control valve (50), and further comprising a monitoring module (60), operably connected to the pneumatic control valve (50), comprising:

an absolute pressure sensor (60d) for measuring at least an absolute pressure (Pabs) in the inner compartment (50f) of the pneumatic control valve (50) and for transmitting at least an absolute pressure signal to a central processing unit (60c), an ambient pressure sensor (60b) for measuring at least an atmospheric pressure (Patm) and for transmitting at least an atmospheric pressure signal to the central processing unit (60c), the central processing unit (60c) specifically programmed and adapted for:
i) processing said absolute pressure signal and atmospheric pressure signal when received from the absolute pressure sensor (60d) and from the ambient pressure sensor (60b), and
ii) determining at least a relative pressure (Pr) in the inner compartment (50f).

2. The artificial resuscitation bag according to claim 1, further comprising a battery unit (60e) for electrically powering the pressure sensors (60b, 60d) and the central processing unit (60c).

3. The artificial resuscitation bag according to claim 1, wherein the central processing unit (60c) is specifically programmed and adapted to calculate the relative pressure (Pr) in the inner compartment (50f) using the following formula:

Pr=Pabs−Patm, wherein:
Pr represents the relative pressure,
Patm represents the atmospheric pressure measured by the atmospheric pressure sensor (60b), and
Pabs represents the absolute pressure measured by the absolute pressure sensor (60d).

4. The artificial resuscitation bag according to claim 1, wherein the pneumatic control valve (50) further comprises a membrane element (50b) cooperating with the exhaust port (50c) adapted to control the flow of gas exiting to the atmosphere through said exhaust port (50c), said membrane element (50b) being arranged into the inner compartment (50f) of the pneumatic control valve (50).

5. The artificial resuscitation bag according to claim 1, wherein an overpressure valve (48) is arranged in the gas conduit (47).

6. The artificial resuscitation bag according to claim 1, wherein the monitoring module (60) is detachably fixed to the pneumatic control valve (50).

7. The artificial resuscitation bag according to claim 1, wherein the monitoring module (60) comprises an electronic board (60a), said absolute pressure sensor (60d), said ambient pressure sensor (60b) and said central processing unit (60c) being arranged on said electronic board (60a).

8. The artificial resuscitation bag according to claim 1, wherein the monitoring module (60) is arranged on a detachable lid structure (70).

9. The artificial resuscitation bag according to claim 4, wherein the inner compartment (50f) is divided into at least a first chamber (50q) and a second chamber (70g) separated by a separating wall (50j) comprising a gas passage (50j) ensuring a fluid communication between said first chamber (50q) and second chamber (70g).

10. The artificial resuscitation bag according to claim 9, wherein the first chamber (50q) of the inner compartment (50f) comprises the membrane element (50b).

11. The artificial resuscitation bag according to claim 9, wherein the second chamber (70g) of the inner compartment (50f) comprises the absolute pressure sensor (60d).

12. The artificial resuscitation bag according to claim 1, further comprising a graphical user interface for displaying the relative pressure (Pr) and/or a thoracic compression rate.

13. An installation for resuscitating a person in state of cardiac arrest comprising:
an artificial resuscitation bag (5) according to claim 1, and
an $O_2$ source fluidly connected to the artificial resuscitation bag (5) by an oxygen line, adapted for providing oxygen to said artificial resuscitation bag (5) during resuscitation.

* * * * *